United States Patent [19]

Föry et al.

[11] Patent Number: 4,579,583
[45] Date of Patent: Apr. 1, 1986

[54] NOVEL SULFONYLUREAS

[75] Inventors: Werner Föry, Basel; Karl Gass, Magden; Willy Meyer, Riehen, all of Switzerland

[73] Assignee: Ciba-Geigy Corporation, Ardsley, N.Y.

[21] Appl. No.: 527,599

[22] Filed: Aug. 29, 1983

[30] Foreign Application Priority Data

Sep. 8, 1982 [CH] Switzerland ............ 5337/82
Apr. 28, 1983 [CH] Switzerland ............ 2283/83

[51] Int. Cl.$^4$ .................. C07D 401/12; A01N 47/36
[52] U.S. Cl. .................................. 71/92; 71/93;
544/113; 544/122; 544/123; 544/209; 544/212;
544/320; 544/324; 544/331
[58] Field of Search ............ 544/332, 331, 320, 324, 544/122, 123; 71/92

[56] References Cited

U.S. PATENT DOCUMENTS 4,419,121 12/1983 Meyer et al. .................. 71/92
4,425,154 1/1984 Meyer et al. .................. 71/92
4,456,469 6/1984 Adams .......................... 71/93

Primary Examiner—Robert Gerstl
Attorney, Agent, or Firm—Edward McC. Roberts; Michael W. Glynn; Frederick H. Rabin

[57] ABSTRACT

The invention relates to N-pyridylsulfonyl-N'-pyrimidinyl- and -N'-triazinylureas of the formula I

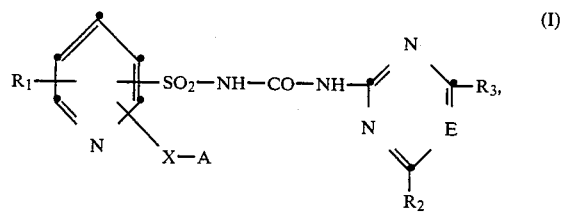

wherein A is a $C_3$–$C_6$alkynyl radical, a $C_1$–$C_6$alkyl radical which is substituted by halogen, $C_1$–$C_4$alkoxy, $C_1$–$C_4$alkylthio, $C_1$–$C_4$alkylsulfinyl, $C_1$–$C_4$alkylsulfonyl, $C_1$–$C_4$haloalkoxy, $C_1$–$C_4$haloalkylthio, $C_1$–$C_4$haloalkylsulfinyl or $C_1$–$C_4$haloalkylsulfonyl, or is a $C_2$–$C_4$alkenyl radical which is unsubstituted or substituted as for $C_1$–$C_6$alkyl, or is a phenyl radical which is unsubstituted or substituted by halogen, cyano, nitro, $C_1$–$C_4$alkyl, $C_1$–$C_4$haloalkyl, an —X—$C_1$–$C_4$alkyl, $C_1$–$C_4$alkoxycarbonyl, amino, mono- or di-($C_1$–$C_4$alkyl)amino, carbamoyl, mono- or di-($C_1$–$C_4$alkyl)carbamoyl, sulfamoyl, mono- or di-($C_1$–$C_4$alkyl)sulfamoyl radical or A—X— forms an amino radical —$NR_6R_7$, E is the methine group or nitrogen, $R_1$ is hydrogen, halogen, $C_1$–$C_4$alkyl, $C_1$–$C_4$alkoxy, $C_1$–$C_4$haloalkyl, $C_1$–$C_4$haloalkoxy, $C_2$–$C_5$alkoxyalkoxy, $C_1$–$C_5$alkylthio, $C_1$–$C_5$alkylsulfinyl or $C_1$–$C_5$alkylsulfonyl, $R_2$ is $C_1$–$C_3$alkyl which is unsubstituted or substituted by 1 to 3 halogen atoms, or is $C_1$–$C_3$alkoxy, $R_3$ is hydrogen, halogen, an amino group —$NR_4R_5$, or $C_1$–$C_3$alkyl which is unsubstituted or substituted by 1 to 3 halogen atoms, or is $C_1$–$C_4$alkoxy which is unsubstituted or substituted by methoxy, ethoxy or 1 to 3 halogen atoms, $R_4$ is hydrogen or methyl, $R_5$ is hydrogen, $C_1$–$C_2$alkyl or methoxy, $R_6$ and $R_7$ are each independently hydrogen, $C_1$–$C_4$alkyl, $C_3$–$C_6$alkenyl, $C_3$–$C_6$alkynyl, $C_3$–$C_6$alkoxyalkyl, $C_1$–$C_4$cyanoalkyl, or both together with the nitrogen atom to which they are attached also form a saturated 5- or 6-membered heterocyclic ring system which may also contain oxygen, sulfur or an —$NR_8$ radical, $R_8$ is hydrogen, $C_1$–$C_4$alkyl or benzyl, and X is oxygen, sulfur, or a sulfinyl or sulfonyl bridge and to the salts thereof with amines, alkali metal bases or alkaline earth metal bases. These compounds have good pre- and postemergence selective herbicidal and growth regulating properties.

17 Claims, No Drawings

NOVEL SULFONYLUREAS

The present invention relates to novel N-pyridylsulfonyl-N'-pyrimidinyl- and N'-triazinylureas with herbicidal and growth regulating properties, to the preparation thereof, to compositions containing them, and to the use thereof for controlling weeds, in particular selectively, in crops of useful plants or for regulating and inhibiting plant growth.

The N-pyridylsulfonyl-N'-pyrimidinyl- and -N'-triazinylureas, and the salts thereof, have the formula I

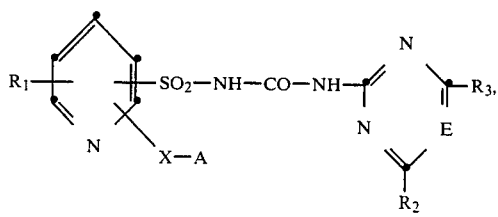

wherein

A is a $C_3$–$C_6$alkynyl radical, a $C_1$–$C_6$alkyl radical which is substituted by halogen, $C_1$–$C_4$alkoxy, $C_1$–$C_4$alkylthio, $C_1$–$C_4$alkylsulfinyl, $C_1$–$C_4$alkylsulfonyl, $C_1$–$C_4$haloalkoxy, $C_1$–$C_4$haloalkylthio, $C_1$–$C_4$haloalkylsulfinyl or $C_1$–$C_4$haloalkylsulfonyl, or is a $C_2$–$C_4$alkenyl radical which is unsubstituted or substituted as for $C_1$–$C_6$alkyl, or is a phenyl radical which is unsubstituted or substituted by halogen, cyano, nitro, $C_1$–$C_4$alkyl, $C_1$–$C_4$haloalkyl, an —X—$C_1$–$C_4$alkyl, $C_1$–$C_4$alkoxycarbonyl, amino, mono- or di-($C_1$–$C_4$alkyl)amino, carbamoyl, mono- or di-($C_1$–$C_4$alkyl)carbamoyl, sulfamoyl, mono- or di-($C_1$–$C_4$alkyl)sulfamoyl radical or A—X— forms an amino radical —$NR_6R_7$, E is the methine group or nitrogen, $R_1$ is hydrogen, halogen, $C_1$–$C_4$alkyl, $C_1$–$C_4$alkoxy, $C_1$–$C_4$haloalkyl, $C_1$–$C_4$haloalkoxy, $C_2$–$C_5$alkoxyalkoxy, $C_1$–$C_5$alkylthio, $C_1$–$C_5$alkylsulfinyl or $C_1$–$C_5$alkylsulfonyl, $R_2$ is $C_1$–$C_3$alkyl which is unsubstituted or substituted by 1 to 3 halogen atoms, or is $C_1$–$C_3$alkoxy, $R_3$ is hydrogen, halogen, an amino group —$NR_4R_5$, or $C_1$–$C_3$alkyl which is unsubstituted or substituted by 1 to 3 halogen atoms, or is $C_1$–$C_4$alkoxy which is unsubstituted or substituted by methoxy, ethoxy or 1 to 3 halogen atoms, $R_4$ is hydrogen or methyl, $R_5$ is hydrogen, $C_1$–$C_2$alkyl or methoxy, $R_6$ and $R_7$ are each independently hydrogen, $C_1$–$C_4$alkyl, $C_3$–$C_6$alkenyl, $C_3$–$C_6$alkynyl, $C_3$–$C_6$alkoxyalkyl, $C_1$–$C_4$cyanoalkyl, or both together with the nitrogen atom to which they are attached also form a saturated 5- or 6-membered heterocyclic ring system which may also contain oxygen, sulfur or an —$NR_8$ radical, $R_8$ is hydrogen, $C_1$–$C_4$alkyl or benzyl, and X is oxygen, sulfur, or a sulfinyl or sulfonyl bridge, with the proviso, that if —X—A forms a $C_3$–$C_4$alkenylsulfide, -sulfinyl or -sulfonyl radical, and $R_1$ is simultaneously hydrogen, halogen, methyl, methoxy, trifluoromethyl, nitro, cyano or methoxymethyl, then the substituent $R_2$ must be $C_1$–$C_2$alkyl, $C_1$–$C_2$alkoxy or methoxymethyl and $R_3$ methyl or methoxy.

Herbicidally active ureas, triazines and pyrimidines are generally known in the art. Pyridylsulfamoyl-heterocyclyl-aminocarbamoyl compounds with herbicidal and plant growth-regulating action have recently been described e.g. in European patent application Nos. 13480 and 35893.

In the above definitions, alkyl denotes straight-chain or branched alkyl, e.g. methyl, ethyl, n-propyl, isopropyl, the four isomers of butyl, and n-amyl, isoamyl, 2-amyl, 3-amyl, n-hexyl or isohexyl.

Alkoxy denotes methoxy, ethoxy, n-propoxy, isopropoxy and the four isomers of butoxy, with methoxy, ethoxy or isopropoxy being preferred.

Alkylthio is e.g. methylthio, ethylthio, n-propylthio, isopropylthio and n-butylthio, with methylthio and ethylthio being preferred.

Alkenyl radicals are e.g. vinyl, allyl, isopropenyl, propen-1-yl, buten-1-yl, buten-2-yl, buten-3-yl, isobuten-1-yl, isobuten-2-yl, penten-1-yl, penten-2-yl, penten-3-yl, penten-4-yl, with vinyl, allyl and penten-4-yl being preferred.

Alkylsulfinyl is e.g. methylsulfinyl, ethylsulfinyl, n-propylsulfinyl and n-butylsulfinyl. Preferred identities are methylsulfinyl and ethylsulfinyl.

Halogen in the above definitions, as well as moiety of haloalkyl, haloalkoxy, haloalkylsulfinyl, haloalkylsulfonyl and haloalkylthio, is fluorine, chlorine and bromine, with fluorine and chlorine being preferred.

Accordingly, haloalkyl or haloalkyl moieties of the substituents defined above will be understood as comprising: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, with chloromethyl, difluoromethyl and trifluoromethyl being preferred.

Alkynyl radicals in the above definitions are generally propargyl, butyn-2-yl, butyn-3-yl, as well as isomers of pentynyl and hexanyl radicals. Preferably, however, alkynyl is propargyl or butyn-2- or 3-yl.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four isomers of butylamine, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which (a) $R_1$ is hydrogen,
(b) $R_1$ is hydrogen and X is oxygen or sulfur, or
(c) compounds of the formula

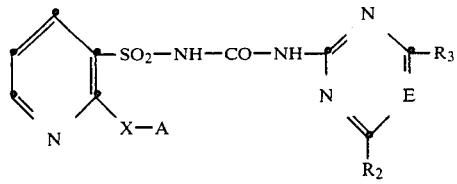

(d) compounds of the above formula in which X is oxygen,
(e) the N-pyridylsulfonyl-N'-pyrimidinylureas of the formula

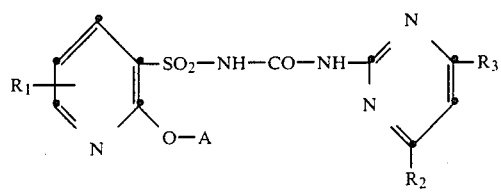

(f) the N-pyridylsulfonyl-N'-triazinylureas of the formula

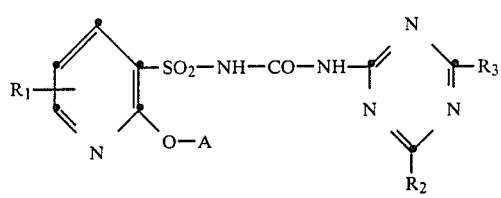

(g) the N-pyridylsulfonylureas of the formula

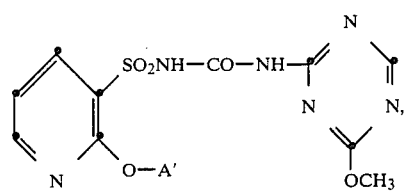

in which A' is $C_3$–$C_4$alkenyl or $C_3$–$C_4$alkoxyalkyl.

In the formulae above, A, E, $R_1$, $R_2$, $R_3$ and X are as defined for formula I.

The process for obtaining the compounds of formula I is carried out in an inert organic solvent.

A first process for obtaining the N-pyridylsulfonyl-N'-pyrimidinyl- or -N'-triazinylureas of the formula I comprises reacting a pyridylsulfonamide of the formula II

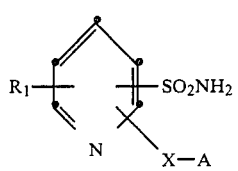

wherein A, $R_1$ and X are as defined for formula I, with an N-pyrimidinyl- or N-triazinylcarbamate of the formula III

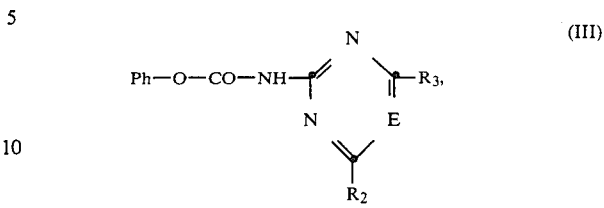

wherein $R_2$, $R_3$ and E are as defined for formula I and Ph is phenyl or phenyl substituted by halogen or alkyl, in the presence of a base.

A second process for obtaining the N-pyridylsulfonyl-N'-pyrimidinyl- and N'-triazinylureas of the formula I comprises reacting a pyridylsulfonyl isocyanate of the formula IV

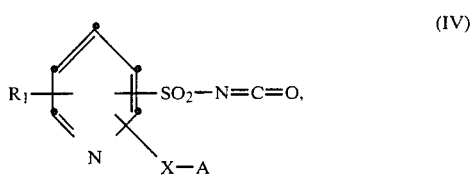

wherein A, $R_1$ and X are as defined for formula I, with an amine of the formula V

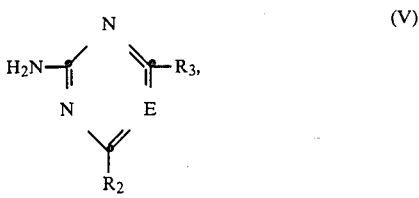

wherein E, $R_2$ and $R_3$ are as defined for formula I, optionally in the presence of a base.

A third process for obtaining the N-pyridylsulfonyl-N'-pyrimidinyl- and -N'-triazinylureas of the formula I comprises reacting a pyridylsulfonylcarbamate of the formula VI

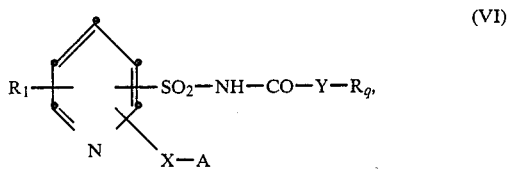

wherein $R_q$ is phenyl or phenyl substituted by halogen or $C_1$–$C_4$alkyl, or is $C_1$–$C_4$alkyl or $C_2$–$C_8$alkoxyalkyl, Y is sulfur or oxygen, and A, $R_1$ and X are as defined for formula I, with an amine of the formula V, in the presence of a base as acid acceptor.

If desired, the urea of formula I may be converted into acid addition salts by reaction with amines, alkali metal hydroxides or alkaline earth metal hydroxides or with quaternary ammonium bases, for example by reacting them with an equimolar amount of base and removing the solvent by evaporation.

The starting materials of the formula II, IV and VI are novel compounds. These compounds and their preparation likewise constitute objects of the invention.

The pyridylsulfonamides of the formula II can be obtained by diazotising a suitably substituted pyridylamine and replacing the diazo group with sulfur dioxide in the presence of a catalyst such as copper(I) chloride, in hydrochloric acid or acetic acid, and reacting the resultant pyridylsulfonyl chloride with ammonia. Corresponding pyridylamines are known or can be prepared by known methods. In specific cases, e.g. where an activated substitution position is available, direct sulfochlorination of the pyridine ring is possible, giving the corresponding pyridylsulfonyl chloride by reaction with an excess of chlorosulfonic acid. Similar reactions of alkoxyanilides are described e.g. in European patent application 44 807.

The pyridylsulfonamides of the formula II can also be obtained by a modification of a method described in J. Med. Chem. 23, 1376 (1980) which comprises chlorinating a suitably substituted mercaptopyridine with chlorine gas in aqueous solution. The pyridylsulfonyl chloride so obtained is reacted with ammonia to give the pyridylsulfonamide.

By employing a modification of a process described in Ann. Pharm. Fr. 31, 467 (1973) it is possible to treat a suitably substituted pyridine ring first with oleum and then with phosphorus pentachloride, optionally in the presence of an inert solvent, to obtain the pyridylsulfonyl chloride, which is then reacted with ammonia to give the pyridylsulfonamide of the formula II.

The novel pyridylsulfonamides of the formula II can also be obtained by reacting a pyridylsulfonamide, which is halogenated at a suitable position, with an alcohol, a thiol or a sulfinyl or sulfonyl compound, in the presence of a base, in accordance with the equation:

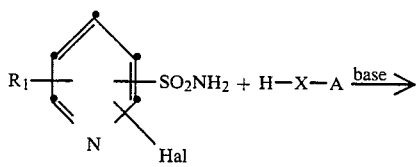

wherein A, $R_1$ and X are as defined for formula I. Particulars on such reactions may be found in J. Pharm, Belg. 35, 98 (1980).

The novel pyridylsulfonamides of the formula II are further obtained by reacting a hydroxypyridyl- or mercaptopyridylsulfonamide with a halide, in the presence of an inert solvent and a base as acid acceptor, in accordance with the equation:

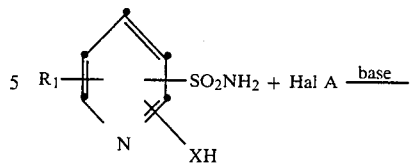

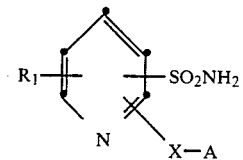

wherein A, $R_1$ and X are as defined for formula I and Hal is a halogen atom, in particular a chlorine or bromine atom. Such reactions are described e.g. in published European patent application No. 44 807.

In addition, it is also possible to obtain the pyridylsulfonamides, wherein X is the sulfonyl or sulfonyl bridge, by oxidising the corresponding thiol compound. Such oxidations are described e.g. in published European patent application No. 35 893.

The sulfonylisocyanates of the formula IV can be obtained by phosgenating the sulfonamides of the formula II, in the presence of butylisocyanate, in a chlorinated hydrocarbon as solvent, at reflux temperature. Similar reactions are described in "Newer Methods of Preparative Organic Chemistry", Vol. VI, 223–241, Academic Press, New York and London.

The pyridylsulfonylcarbamates of the formula VI are obtained by reacting the sulfonamides of the formula II with diphenyl carbonate or phenyl chloroformate in the presence of a base. Similar processes are described in Japanese patent specification No. 61 169.

The aminopyrimidines and aminotriazines of the formula V employed as starting materials, as well as corresponding phenylcarbamates of the formula III, are either well known or described in Swiss patent application No. 3527/82-8, or they can be prepared by known methods from compounds described therein.

It is convenient to carry out the reactions for obtaining compounds of formula I in aprotic, inert organic solvents such as methylene chloride, tetrahydrofuran, acetonitrile, dioxan, or toluene.

The reaction temperatures are preferably in the range from −20° to +120° C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The compounds of formula I are stable compounds and no protective measures are required for handling them.

When used in low rates of application, the compounds of formula I have good selective growth inhibiting and selective herbicidal properties which make them most suitable for use in crops of useful plants,

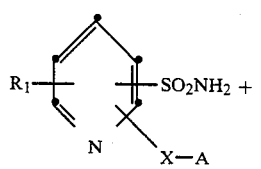

especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used in very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipides.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1964.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

Emulsifiable concentrates active ingredient: 1 to 20%, preferably 5 to 10%
surfactant: 5 to 30%, preferably 10 to 20%
liquid carrier: 50 to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 0.5 to 90%, preferably 10 to 80%
surfactant: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples.

EXAMPLE 1

Preparation of N-[2-(2-methoxyethoxy)-3-pyridylsulfonyl]-N'-[4-methoxy-6-methyl-1,3,5-triazin-2-yl]urea of the formula

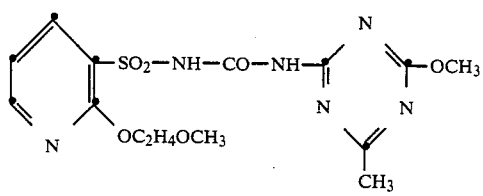

5.2 g of N-(4-methoxy-6-methyl-1,3,5-triazin-2-yl)phenylcarbamate are added at a maximum temperature of 22° C. to a mixture of 4.64 g of 2-(2-methoxy)-3-pyridylsulfonamide in 3.1 ml of 1,8-diazabicyclo[5.4.0]undec-7-ene in 50 ml of absolute dioxan. The mixture is stirred for 1 hour at room temperature, concentrated in vacuo, and the residue is stirred in 12 ml of 2N aqueous HCl and filtered. The residue is washed with water and dried, affording 7.9 g of the title urea with a melting point of 112°–114° C.

The starting 2-(2-methoxyethoxy)-3-pyridylsulfonamide is prepared as follows:

4.36 g of a 55% dispersion of sodium in oil is added in portions over 15 minutes and under nitrogen to 25 ml of methyl cellosolve. A solution of 9.6 g of 2-chloro-3-pyridylsulfonamide in 25 ml of methyl cellosolve is then added dropwise, with stirring, to the above dispersion over 5 minutes. The reaction mixture is then stirred for 1 hour at reflux temperature and concentrated in vacuo. The residue is acidified to pH 2 with about 25 ml of aqueous HCl at a temperature below 15° C., then stirred and filtered, affording 11.3 g of the desired 2-(2-methoxyethoxy)-3-pyridylsulfonamide, which is recrystallised from acetonitrile and has a melting point of 102°–103° C.

EXAMPLE 2

Preparation of N-[2-dimethylamino-3-pyridylsulfonyl]-N'-[4-methoxy-6-methyl-1,3,5-triazin-2-yl]urea of the formula

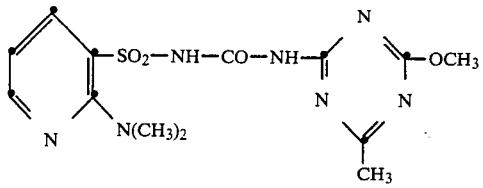

3.28 g of N-(4-methoxy-6-methyl-1,3,5-triazin-2-yl)phenylcarbamate are added at room temperature to a mixture of 2.41 g of 2-dimethylamino-3-pyridylsulfonamide and 1.9 ml of 1,7-diazabicyclo[5.4.0]undec-7-ene in 30 ml of absolute dioxan. The mixture is stirred for 1 hour at this temperature and then concentrated in vacuo. The residue is stirred in 10 ml of 1N aqueous HCl and filtered. The filter residue is washed with water and ether and dried, affording 3.94 g of the title urea with a melting point 173°–175° C.

The starting 2-dimethylamino-3-pyridylsulfonamide is prepared as follows:

6.32 g of dimethylamine is introduced at 0° C. into a pressure reactor containing 6.73 g of 2-chloro-3-pyridylsulfonamide in 60 ml of absolute tetrahydrofuran. The contents of the reactor are stirred for 75 minutes at 60° C., then cooled and filtered. The filtrated is concentrated in vacuo and the residue is stirred in a 1:1 mixture of ether/petroleum ether and filtered, affording 6.32 g of the above sulfonamide with a melting point 98°–100° C.

EXAMPLE 3

Preparation of N-[2-phenoxy-3-pyridylsulfonyl]-N'-[4-methoxy-6-methyl-1,3,5-triazin-2-yl]urea of the formula

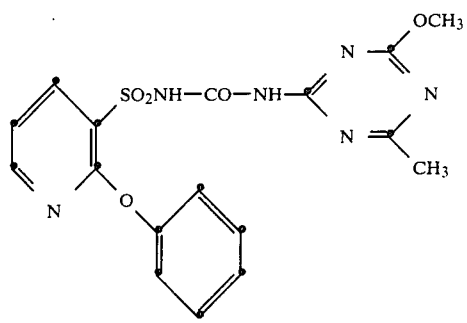

(a) 2.08 g of N-(4-methoxy-6-methyl-1,3,5-triazin-2-yl)phenylcarbamate are added at 25° C. to a mixture of 2 g of 2-phenoxy-3-pyridylsulfonamide and 1.4 ml of 1,8-diazabicyclo[5.4.0]undec-7-ene in 25 ml of absolute acetonitrile. The mixture is stirred for 20 hours at room temperature and then poured into 150 ml of HCl and ice. The precipitate is isolated by filtration, washed with water, dried and crystallised from ethyl acetate, affording 2 g of the title urea with a melting point of 181°–182° C.

The starting 2-phenoxy-3-pyridylsulfonamide is prepared as follows:

(b) 14 g of KOH powder (88%) are added to a solution of 20.7 g of phenol in 150 ml of dimethylsulfoxide and the mixture is stirred for 1½ hours. A solution of 19.26 g of 2-chloro-3-pyridylsulfonamide in 50 ml of dimethylsulfoxide and 0.1 g of 18-crown-6 are then added and stirring is continued for 44 hours at 130° C. The reaction mixture is poured onto a mixture of 2N HCl and ice and well stirred. The precipitate is isolated by filtration, well washed with water, dried and recrystallised from ethyl acetate. Yield: 17.5 g of the desired 2-phenoxy-3-pyridylsulfonamide with a melting point of 176°–178° C. after recrystallisation from ethyl acetate.

EXAMPLE 4

Preparation of N-[2-allyloxy-3-pyridylsulfonyl]-N'-[4,6-dimethoxy-1,3,5-triazin-2-yl]urea of the formula

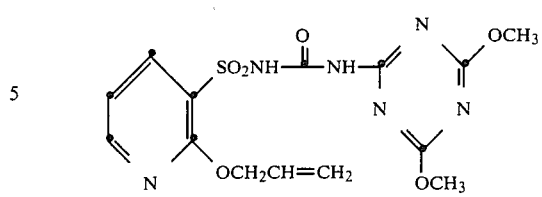

(a) 4.83 g of N-2-allyloxy-3-pyridylsulfonylphenylcarbamate in 30 ml of dioxan are added dropwise at 60° C. over 15 minutes to a mixture of 2.03 g of 2-amino-4,6-dimethoxy-1,3,5-triazine and 0.09 ml of triethylamine in 30 ml of absolute dioxan. The reaction mixture is stirred for 1½ hours at 70° C., filtered warm, and concentrated at 50° C. in vacuo. The oily residue is then triturated with ether and filtered, affording 3.28 g of the desired sulfonylurea with a melting point of 152°–154° C.

The starting N-2-allyloxy-3-pyridylsulfonylphenylcarbamate of the formula

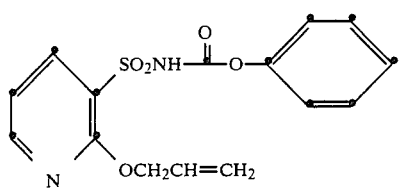

is prepared as follows:

(b) A solution of 4.7 g of diphenylcarbamate in 30 ml of dimethylformamide is added dropwise at a maximum temperature of 20° C. over 5 minutes to a 55% suspension of 0.87 g of sodium hydride in 10 ml of absolute dimethylformamide. A solution of 4.28 g of 2-allyloxy-3-pyridylsulfonamide in 20 ml of dimethylformamide is then added dropwise at a maximum temperature of 20° C. over 20 minutes to the above reaction mixture and the batch is stirred at this temperature for 1 hour. The reaction solution is taken up in a mixture of 130 ml of ethyl acetate, 130 ml of ice-water and 19.2 ml of 2N HCl. The organic phase is separated, washed four times with cold water, dried over sodium sulfate and dried. The residue is triturated with ether, filtered and dried, affording 5.8 g of the desired phenylcarbamate with a melting point of 144°–146° C.

The following ureas are prepared in accordance with the foregoing Examples:

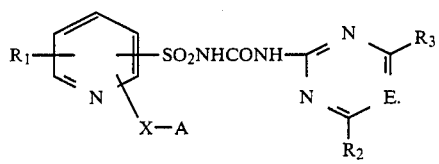

| | | | Position | | | | |
|---|---|---|---|---|---|---|---|
| No. | $R_1$ | X—A | —$SO_2$— | $R_2$ | $R_3$ | E | m.p. °C. |
| 1 | H | 2-$OC_2H_4OCH_3$ | 3 | $CH_3$ | $OCH_3$ | N | 112–114° |
| 2 | H | 2-$OC_2H_4OCH_3$ | 3 | $OCH_3$ | $OCH_3$ | N | |
| 3 | H | 2-$OC_2H_4OCH_3$ | 3 | $OCH_3$ | $N(CH_3)_2$ | N | |
| 4 | H | 2-$OC_2H_4OCH_3$ | 3 | $OCH_3$ | $OCH_2CF_3$ | N | |
| 5 | H | 2-$OC_2H_4OCH_3$ | 3 | $CH_3$ | $CH_3$ | CH | |
| 6 | H | 2-$OC_2H_4OCH_3$ | 3 | $CH_3$ | $OCH_3$ | CH | |
| 7 | H | 2-$OC_2H_4OCH_3$ | 3 | $OCH_3$ | $OCH_3$ | CH | |
| 8 | H | 2-$OC_2H_4OCH_3$ | 3 | $CH_3$ | $OCHF_2$ | CH | 148–150° |
| 9 | H | 2-$OCH_2CH=CH_2$ | 3 | $CH_3$ | $OCH_3$ | N | 158–159° |
| 10 | H | 2-$OCH_2CH=CH_2$ | 3 | $OCH_3$ | $OCH_3$ | N | 152–154° |

-continued

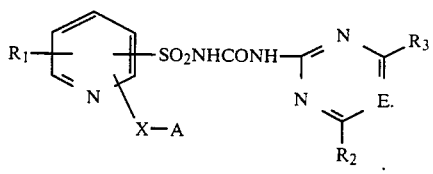

| No. | R₁ | X—A | Position —SO₂— | R₂ | R₃ | E | m.p. °C. |
|---|---|---|---|---|---|---|---|
| 11 | H | 2-OCH₂CH=CH₂ | 3 | OCH₃ | N(CH₃)₂ | N | |
| 12 | H | 2-OCH₂CH=CH₂ | 3 | OCH₃ | —OCH₂CF₃ | N | |
| 13 | H | 2-OCH₂CH=CH₂ | 3 | CH₃ | CH₃ | CH | 184–186° |
| 14 | H | 2-OCH₂CH=CH₂ | 3 | CH₃ | OCH₃ | CH | 182–183° |
| 15 | H | 2-OCH₂CH=CH₂ | 3 | OCH₃ | OCH₃ | CH | |
| 16 | H | 2-OCH₂CH=CH₂ | 3 | CH₃ | OCHF₂ | CH | 158–159° |
| 17 | H | 2-OCH₂—C≡CH | 3 | CH₃ | OCH₃ | N | 161–163° |
| 18 | H | 2-OCH₂—C≡CH | 3 | OCH₃ | OCH₃ | N | |
| 19 | H | 2-OCH₂—C≡CH | 3 | OCH₃ | N(CH₃)₂ | N | |
| 20 | H | 2-OCH₂—C≡CH | 3 | OCH₃ | OCH₂CF₃ | N | |
| 21 | H | 2-OCH₂—C≡CH | 3 | CH₃ | CH₃ | CH | 188–189° (decomp.) |
| 22 | H | 2-OCH₂—C≡CH | 3 | OCH₃ | CH₃ | CH | 150–152° |
| 23 | H | 2-OCH₂—C≡CH | 3 | OCH₃ | OCH₃ | CH | 168–172° |
| 24 | H | 2-OCH₂C≡CH | 3 | CH₃ | OCHF₂ | CH | 179–181° |
| 25 | H | 2-OCH₂C(CH₃)=CH₂ | 3 | CH₃ | OCH₃ | N | 136–137° |
| 26 | H | 2-OCH₂C(CH₃)=CH₂ | 3 | OCH₃ | OCH₃ | N | |
| 27 | H | 2-OCH₂C(CH₃)=CH₂ | 3 | OCH₃ | N(CH₃)₂ | N | 153–155° |
| 28 | H | 2-OCH₂C(CH₃)=CH₂ | 3 | OCH₃ | OCH₂CF₃ | N | 114–116° |
| 29 | H | 2-OCH₂C(CH₃)=CH₂ | 3 | CH₃ | CH₃ | CH | |
| 30 | H | 2-OCH₂C(CH₃)=CH₂ | 3 | OCH₃ | CH₃ | CH | 158–159° |
| 31 | H | 2-OCH₂C(CH₃)=CH₂ | 3 | OCH₃ | OCH₃ | CH | 146–147° |
| 32 | H | 2-OCH₂C(CH₃)=CH₂ | 3 | CH₃ | OCHF₂ | CH | 149–152° |
| 33 | H | 2-OCH₂CH=CHCH₃ | 3 | CH₃ | OCH₃ | N | 168–169° |
| 34 | H | 2-OCH₂CH=CHCH₃ | 3 | OCH₃ | OCH₃ | N | 140–143° |
| 35 | H | 2-OCH₂CH=CHCH₃ | 3 | OCH₃ | N(CH₃)₂ | N | 184–187° |
| 36 | H | 2-OCH₂CH=CHCH₃ | 3 | OCH₃ | OCH₂CF₃ | N | 108–111° |
| 37 | H | 2-OCH₂CH=CHCH₃ | 3 | CH₃ | CH₃ | CH | 148–150° |
| 38 | H | 2-OCH₂CH=CHCH₃ | 3 | OCH₃ | CH₃ | CH | 141–143° |
| 39 | H | 2-OCH₂CH=CHCH₃ | 3 | OCH₃ | OCH₃ | CH | 180–184° |
| 40 | H | 2-OCH₂CH=CHCH₃ | 3 | CH₃ | OCHF₂ | CH | 146–148° |
| 41 | H | 2-OC₂H₄Cl | 3 | CH₃ | OCH₃ | N | 168–172° |
| 42 | H | 2-OC₂H₄Cl | 3 | OCH₃ | OCH₃ | N | |
| 43 | H | 2-OC₂H₄Cl | 3 | OCH₃ | N(CH₃)₂ | N | |
| 44 | H | 2-OC₂H₄Cl | 3 | OCH₃ | OCH₂CF₃ | N | |
| 45 | H | 2-OC₂H₄Cl | 3 | CH₃ | CH₃ | CH | |
| 46 | H | 2-OC₂H₄Cl | 3 | OCH₃ | CH₃ | CH | |
| 47 | H | 2-OC₂H₄Cl | 3 | OCH₃ | OCH₃ | CH | |
| 48 | H | 2-OC₂H₄Cl | 3 | CH₃ | OCHF₂ | CH | 96–100° |
| 49 | H | 2-OCHF₂ | 3 | CH₃ | OCH₃ | N | |
| 50 | H | 2-OCHF₂ | 3 | OCH₃ | OCH₃ | N | |
| 51 | H | 2-OCHF₂ | 3 | OCH₃ | N(CH₃)₂ | N | |
| 52 | H | 2-OCHF₂ | 3 | OCH₃ | OCH₂CF₃ | N | |
| 53 | H | 2-OCHF₂ | 3 | CH₃ | CH₃ | CH | |
| 54 | H | 2-OCHF₂ | 3 | OCH₃ | CH₃ | CH | |
| 55 | H | 2-OCHF₂ | 3 | OCH₃ | OCH₃ | CH | |
| 56 | H | 2-OCHF₂ | 3 | CH₃ | OCHF₂ | CH | |
| 57 | H | 2-OCF₂CHF₂ | 3 | CH₃ | OCH₃ | N | |
| 58 | H | 2-OCF₂CHF₂ | 3 | OCH₃ | OCH₃ | N | |
| 59 | H | 2-OCF₂CHF₂ | 3 | OCH₃ | N(CH₃)₂ | N | |
| 60 | H | 2-OCF₂CHF₂ | 3 | OCH₃ | OCH₂CF₃ | N | |
| 61 | H | 2-OCF₂CHF₂ | 3 | CH₃ | CH₃ | CH | |
| 62 | H | 2-OCF₂CHF₂ | 3 | OCH₃ | CH₃ | CH | |
| 63 | H | 2-OCF₂CHF₂ | 3 | OCH₃ | OCH₃ | CH | |
| 64 | H | 2-OCF₂CHF₂ | 3 | CH₃ | OCHF₂ | CH | |
| 65 | H | 2-SCHF₂ | 3 | CH₃ | OCH₃ | N | |
| 66 | H | 2-SCHF₂ | 3 | OCH₃ | OCH₃ | N | |
| 67 | H | 2-SCHF₂ | 3 | OCH₃ | N(CH₃)₂ | N | |
| 68 | H | 2-SCHF₂ | 3 | OCH₃ | OCH₂CF₃ | N | |
| 69 | H | 2-SCHF₂ | 3 | CH₃ | CH₃ | CH | |
| 70 | H | 2-SCHF₂ | 3 | OCH₃ | CH₃ | CH | |
| 71 | H | 2-SCHF₂ | 3 | OCH₃ | OCH₃ | CH | |
| 72 | H | 2-SCHF₂ | 3 | CH₃ | OCHF₂ | CH | |
| 73 | H | 2-OC₂H₄OCH₃ | 3 | CH₃ | OCH₃ | N | |
| 74 | H | 2-OC₂H₄OCH₃ | 3 | OCH₃ | OCH₃ | N | |
| 75 | H | 2-OC₂H₄OCH₃ | 3 | OCH₃ | N(CH₃)₂ | N | |
| 76 | H | 2-OC₂H₄OCH₃ | 3 | OCH₃ | OCH₂CF₃ | N | |
| 77 | H | 2-OC₂H₄OCH₃ | 3 | CH₃ | CH₃ | CH | |
| 78 | H | 2-OC₂H₄OCH₃ | 3 | OCH₃ | CH₃ | CH | |
| 79 | H | 2-OC₂H₄OCH₃ | 3 | OCH₃ | OCH₃ | CH | |
| 80 | H | 2-OC₂H₄OCH₃ | 3 | CH₃ | OCHF₂ | CH | |
| 81 | H | 4-OC₂H₄OCH₃ | 3 | CH₃ | OCH₃ | N | |

-continued

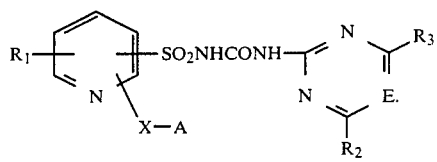

| No. | R₁ | X—A | Position —SO₂— | R₂ | R₃ | E | m.p. °C. |
|---|---|---|---|---|---|---|---|
| 82 | H | 4-OC₂H₄OCH₃ | 3 | OCH₃ | OCH₃ | N | |
| 83 | H | 4-OC₂H₄OCH₃ | 3 | OCH₃ | N(CH₃)₂ | N | |
| 84 | H | 4-OC₂H₄OCH₃ | 3 | OCH₃ | OCH₂CF₃ | N | |
| 85 | H | 4-OC₂H₄OCH₃ | 3 | CH₃ | CH₃ | CH | |
| 86 | H | 4-OC₂H₄OCH₃ | 3 | OCH₃ | CH₃ | CH | |
| 87 | H | 4-OC₂H₄OCH₃ | 3 | OCH₃ | OCH₃ | CH | |
| 88 | H | 4-OC₂H₄OCH₃ | 3 | CH₃ | OCHF₃ | CH | |
| 89 | H | 4-OC₂H₄Cl | 3 | CH₃ | OCH₃ | N | |
| 90 | H | 4-OC₂H₄Cl | 3 | OCH₃ | OCH₃ | N | |
| 91 | H | 4-OC₂H₄Cl | 3 | OCH₃ | N(CH₃)₂ | N | |
| 92 | H | 4-OC₂H₄Cl | 3 | OCH₃ | OCH₂CF₃ | N | |
| 93 | H | 4-OC₂H₄Cl | 3 | CH₃ | CH₃ | CH | |
| 94 | H | 4-OC₂H₄Cl | 3 | OCH₃ | CH₃ | CH | |
| 95 | H | 4-OC₂H₄Cl | 3 | OCH₃ | OCH₃ | CH | |
| 96 | H | 4-OC₂H₄Cl | 3 | CH₃ | OCHF₂ | CH | |
| 97 | H | 4-OCF₂ | 3 | CH₃ | OCH₃ | N | |
| 98 | H | 4-OCF₂ | 3 | OCH₃ | OCH₃ | N | |
| 99 | H | 4-OCF₂ | 3 | OCH₃ | N(CH₃)₂ | N | |
| 100 | H | 4-OCF₂ | 3 | OCH₃ | OCH₂CF₃ | N | |
| 101 | H | 4-OCF₂ | 3 | CH₃ | CH₃ | CH | |
| 102 | H | 4-OCF₂ | 3 | OCH₃ | CH₃ | CH | |
| 103 | H | 4-OCF₂ | 3 | OCH₃ | OCH₃ | CH | |
| 104 | H | 4-OCF₂ | 3 | CH₃ | OCHF₃ | CH | |
| 105 | H | 4-OCH₂C≡CH | 3 | CH₃ | OCH₃ | N | |
| 106 | H | 4-OCH₂C≡CH | 3 | OCH₃ | OCH₃ | N | |
| 107 | H | 4-OCH₂C≡CH | 3 | OCH₃ | N(CH₃)₂ | N | |
| 108 | H | 4-OCH₂C≡CH | 3 | OCH₃ | OCH₂CF₃ | N | |
| 109 | H | 4-OCH₂C≡CH | 3 | CH₃ | CH₃ | CH | |
| 110 | H | 4-OCH₂C=CH | 3 | OCH₃ | CH₃ | CH | |
| 111 | H | 4-OCH₂C≡CH | 3 | OCH₃ | OCH₃ | CH | |
| 112 | H | 4-OCH₂C≡CH | 3 | CH₃ | OCHF₃ | CH | |
| 113 | 6-CH₃ | 2-OCH₂CH=CH₂ | 3 | CH₃ | OCH₃ | N | |
| 114 | 6-CH₃ | 2-OCH₂CH=CH₂ | 3 | OCH₃ | OCH₃ | N | |
| 115 | 6-CH₃ | 2-OCH₂CH=CH₂ | 3 | OCH₃ | N(CH₃)₂ | N | |
| 116 | 6-CH₃ | 2-OCH₂CH=CH₂ | 3 | OCH₃ | OCH₂CF₃ | N | |
| 117 | 6-CH₃ | 2-OCH₂CH=CH₂ | 3 | CH₃ | CH₃ | CH | |
| 118 | 6-CH₃ | 2-OCH₂CH=CH₂ | 3 | OCH₃ | CH₃ | CH | |
| 119 | 6-CH₃ | 2-OCH₂CH=CH₂ | 3 | OCH₃ | OCH₃ | CH | |
| 120 | 6-CH₃ | 2-OCH₂CH=CH₂ | 3 | OCH₃ | OCHF₂ | CH | |
| 121 | 6-CH₃ | 2-OC₂H₄OCH₃ | 3 | CH₃ | OCH₃ | N | |
| 122 | 6-CH₃ | 2-OC₂H₄OCH₃ | 3 | OCH₃ | OCH₃ | N | |
| 123 | 6-CH₃ | 2-OC₂H₄OCH₃ | 3 | OCH₃ | N(CH₃)₂ | N | |
| 124 | 6-CH₃ | 2-OC₂H₄OCH₃ | 3 | OCH₃ | OCH₂CF₃ | N | |
| 125 | 6-CH₃ | 2-OC₂H₄OCH₃ | 3 | CH₃ | CH₃ | CH | |
| 126 | 6-CH₃ | 2-OC₂H₄OCH₃ | 3 | OCH₃ | CH₃ | CH | |
| 127 | 6-CH₃ | 2-OC₂H₄OCH₃ | 3 | OCH₃ | OCH₃ | CH | |
| 128 | 6-CH₃ | 2-OC₂H₄OCH₃ | 3 | CH₃ | OCHF₂ | CH | |
| 129 | 6-CH₃ | 2-OCHF₂ | 3 | CH₃ | OCH₃ | N | |
| 130 | 6-CH₃ | 2-OCHF₂ | 3 | OCH₃ | OCH₃ | N | |
| 131 | 6-CH₃ | 2-OCHF₂ | 3 | OCH₃ | N(CH₃)₂ | N | |
| 132 | 6-CH₃ | 2-OCHF₂ | 3 | OCH₃ | OCH₂CF₃ | N | |
| 133 | 6-CH₃ | 2-OCHF₂ | 3 | CH₃ | CH₃ | CH | |
| 134 | 6-CH₃ | 2-OCHF₂ | 3 | OCH₃ | CH₃ | CH | |
| 135 | 6-CH₃ | 2-OCHF₂ | 3 | OCH₃ | OCH₃ | CH | |
| 136 | 6-CH₃ | 2-OCHF₂ | 3 | CH₃ | OCHF₂ | CH | |
| 137 | 6-CH₃ | 3-OCHF₂ | 2 | CH₃ | OCH₃ | N | |
| 138 | 6-CH₃ | 3-OCHF₂ | 2 | OCH₃ | OCH₃ | N | |
| 139 | 6-CH₃ | 3-OCHF₂ | 2 | OCH₃ | N(CH₃)₂ | N | |
| 140 | 6-CH₃ | 3-OCHF₂ | 2 | OCH₃ | OCH₂CF₃ | N | |
| 141 | 6-CH₃ | 3-OCHF₂ | 2 | CH₃ | OCH₃ | CH | |
| 142 | 6-CH₃ | 3-OCHF₂ | 2 | OCH₃ | OCH₃ | CH | |
| 143 | 6-CH₃ | 3-OCHF₂ | 2 | OCH₃ | OCH₃ | CH | |
| 144 | 6-CH₃ | 3-OCHF₂ | 2 | CH₃ | OCHF₂ | CH | |
| 145 | H | 2-SO₂C₂H₄OCH₃ | 3 | CH₃ | OCH₃ | N | |
| 146 | H | 2-SO₂C₂H₄OCH₃ | 3 | OCH₃ | OCH₃ | N | |
| 147 | H | 2-SO₂C₂H₄OCH₃ | 3 | OCH₃ | N(CH₃)₂ | N | |
| 148 | H | 2-SO₂C₂H₄OCH₃ | 3 | OCH₃ | OCH₂CF₃ | N | |
| 149 | H | 2-SO₂C₂H₄OCH₃ | 3 | CH₃ | CH₃ | CH | |
| 150 | H | 2-SO₂C₂H₄OCH₃ | 3 | OCH₃ | CH₃ | CH | |
| 151 | H | 2-SO₂C₂H₄OCH₃ | 3 | OCH₃ | OCH₃ | CH | |
| 152 | H | 2-SO₂C₂H₄OCH₃ | 3 | CH₃ | OCHF₂ | CH | |

-continued

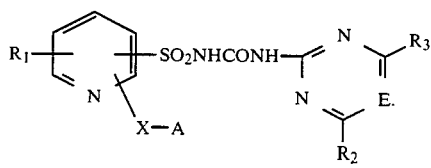

|     |       |          | Position |                   |                    |    |          |
|-----|-------|----------|----------|-------------------|--------------------|-----|----------|
| No. | $R_1$ | X—A      | —$SO_2$— | $R_2$             | $R_3$              | E   | m.p. °C. |
| 153 | H | 2-$NH_2$ | 3 | $CH_3$ | $OCH_3$ | N | 194–195° |
| 154 | H | 2-$NH_2$ | 3 | $OCH_3$ | $OCH_3$ | N | |
| 155 | H | 2-$NH_2$ | 3 | $OCH_3$ | $OCH_3$ | CH | |
| 156 | H | 2-$NH_2$ | 3 | $OCH_3$ | $CH_3$ | CH | |
| 157 | H | 2-$NH_2$ | 3 | $OCHF_2$ | $CH_3$ | CH | |
| 158 | H | 2-$NHCH_3$ | 3 | $OCHF_2$ | $CH_3$ | CH | |
| 159 | H | 2-$NHCH_3$ | 3 | $OCH_3$ | $CH_3$ | CH | |
| 160 | H | 2-$NHCH_3$ | 3 | $CH_3$ | $CH_3$ | CH | |
| 161 | H | 2-$NHCH_3$ | 3 | $CH_3$ | $OCH_3$ | N | 147–148° |
| 162 | H | 2-$N(CH_3)_2$ | 3 | $CH_3$ | $OCH_3$ | N | 173–175° |
| 163 | H | 2-$N(CH_3)_2$ | 3 | $OCH_3$ | $OCH_3$ | N | |
| 164 | H | 2-$N(CH_3)_2$ | 3 | $CH_3$ | $OC_2H_5$ | N | |
| 165 | H | 2-$N(CH_3)_2$ | 3 | $OCH_3$ | $N(CH_3)_2$ | N | |
| 166 | H | 2-$N(CH_3)_2$ | 3 | $OCH_3$ | $CH_3$ | CH | |
| 167 | H | 2-$N(CH_3)_2$ | 3 | $OCH_3$ | $OCH_3$ | CH | |
| 168 | H | 2-$N(CH_3)_2$ | 3 | $CH_3$ | $OCHF_2$ | CH | |
| 169 | H | 2-$N(CH_3)_2$ | 3 | $CH_3$ | $CH_3$ | CH | |
| 170 | H | 2-$N(CH_2CH=CH_2)_2$ | 3 | $CH_3$ | $OCH_3$ | N | 120–122° |
| 171 | H | 2-$N(CH_2CH=CH_2)_2$ | 3 | $CH_3$ | $OCH_3$ | CH | 161–163° |
| 172 | H | 2-$N(CH_2CH=CH_2)_2$ | 3 | $CH_3$ | $OCHF_2$ | CH | 113–122° |
| 173 | H | 2-$N(CH_2CH=CH_2)_2$ | 3 | $OCH_3$ | $OCH_3$ | N | 126–128° |
| 174 | H | 2-$N(CH_2CH=CH_2)_2$ | 3 | $OCH_3$ | $OCH_3$ | CH | 145–149° |
| 175 | H | 2-$N(CH_2CH=CH_2)_2$ | 3 | $CH_3$ | $OC_2H_5$ | N | 165–167° |
| 176 | H | 2-$N(CH_2CH=CH_2)_2$ | 3 | $CH_3$ | $CH_3$ | CH | 180–182° |
| 177 | H | 2-$N(CH_2CH=CH_2)_2$ | 3 | $OCH_3$ | $OCH_2CF_3$ | N | 127–130° |
| 178 | H | 2-piperidino | 3 | $CH_3$ | $OCH_3$ | N | 177–179° |
| 179 | H | 2-piperidino | 3 | $OCH_3$ | $OCH_3$ | CH | 162–165° |
| 180 | H | 2-piperidino | 3 | $OCH_3$ | $CH_3$ | CH | 186–191° |
| 181 | H | 2-piperidino | 3 | $OCH_3$ | $OCH_3$ | N | 179–181° |
| 182 | H | 2-morpholino | 3 | $CH_3$ | $OCH_3$ | N | 185–186° |
| 183 | H | 2-morpholino | 3 | $CH_3$ | $OCH_3$ | CH | 186–189° |
| 184 | H | 2-morpholino | 3 | $OCH_3$ | $OCH_3$ | CH | 170–173° |
| 185 | H | 2-morpholino | 3 | $OCH_3$ | $OCH_3$ | N | 100–102° |
| 186 | H | 2-morpholino | 3 | $OCHF_2$ | $CH_3$ | CH | 184–187° |
| 187 | H | 2-(4′-methyl-piperazino) | 3 | $OCHF_2$ | $CH_3$ | CH | 172–175° |
| 188 | H | 2-(4′-methyl-piperazino) | 3 | $OCH_3$ | $CH_3$ | CH | 177–179° |
| 189 | H | 2-(4′-methyl-piperazino) | 3 | $CH_3$ | $CH_3$ | CH | 159–162° |
| 190 | H | 2-(4′-methyl-piperazino) | 3 | $CH_3$ | $OCH_3$ | N | 158° |
| 191 | H | 2-(4′-methyl-piperazino) | 3 | $OCH_3$ | $OCH_3$ | N | |
| 192 | H | 2-(4′-methyl-piperazino) | 3 | $OCH_3$ | $OCH_3$ | CH | 156–159° |
| 193 | H | 2-phenoxy | 3 | $CH_3$ | $OCH_3$ | N | 181–182° |
| 194 | H | 2-phenoxy | 3 | $CH_3$ | $OCH_3$ | CH | 188–189° |
| 195 | H | 2-phenoxy | 3 | $OCH_3$ | $OCH_3$ | N | |
| 196 | H | 2-phenoxy | 3 | $OCH_3$ | $N(CH_3)_2$ | N | |
| 197 | H | 2-phenoxy | 3 | $CH_3$ | $CH_3$ | CH | |
| 198 | H | 2-phenoxy | 3 | $OCH_3$ | $OCH_3$ | CH | |
| 199 | H | 2-phenoxy | 3 | $CH_3$ | $OCHF_2$ | CH | |
| 200 | 5-Cl | 2-phenoxy | 3 | $CH_3$ | $OCH_3$ | N | |
| 201 | 5-Cl | 2-phenoxy | 3 | $CH_3$ | $OCH_3$ | CH | |
| 202 | H | 2-(2′-fluorophenoxy) | 3 | $CH_3$ | $OCH_3$ | N | |
| 203 | H | 2-(2′-fluorophenoxy) | 3 | $CH_3$ | $OCH_3$ | CH | |
| 204 | H | 2-(2′-fluorophenoxy) | 3 | $OCH_3$ | $OCH_3$ | CH | |
| 205 | H | 2-(3′-fluorophenoxy) | 3 | $CH_3$ | $OCH_3$ | N | |
| 206 | H | 2-(3′-fluorophenoxy) | 3 | $CH_3$ | $OCH_3$ | CH | |
| 207 | H | 2-(3′-fluorophenoxy) | 3 | $OCH_3$ | $OCH_3$ | CH | |
| 208 | H | 2-m-tolyloxy | 3 | $OCH_3$ | $OCH_3$ | CH | |
| 209 | H | 2-m-tolyloxy | 3 | $CH_3$ | $OCH_3$ | CH | |
| 210 | H | 2-m-tolyloxy | 3 | $CH_3$ | $OCH_3$ | N | |
| 211 | H | 2-phenylthio | 3 | $CH_3$ | $OCH_3$ | N | |
| 212 | H | 2-phenylthio | 3 | $CH_3$ | $OCH_3$ | N | |
| 213 | H | 2-phenylthio | 3 | $CH_3$ | $OCH_3$ | CH | |
| 214 | H | 2-phenylthio | 3 | $OCH_3$ | $OCH_3$ | CH | |
| 215 | H | 2-phenylthio | 3 | $CH_3$ | $OCHF_2$ | CH | |
| 216 | H | 3-phenoxy | 2 | $CH_3$ | $OCH_3$ | N | |
| 217 | H | 3-phenoxy | 2 | $OCH_3$ | $OCH_3$ | N | |

-continued

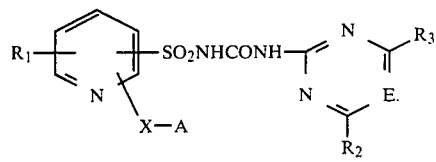

| No. | R₁ | X—A | Position —SO₂— | R₂ | R₃ | E | m.p. °C. |
|---|---|---|---|---|---|---|---|
| 218 | H | 3-phenoxy | 2 | CH₃ | OCH₃ | CH | |
| 219 | H | 3-phenoxy | 2 | OCH₃ | OCH₃ | CH | |
| 220 | H | 3-phenoxy | 2 | CH₃ | CH₃ | CH | |
| 221 | H | 3-phenoxy | 2 | CH₃ | OCHF₂ | CH | |
| 222 | H | 3-phenoxy | 2 | OCH₃ | N(CH₃)₂ | N | |
| 223 | 5-Cl | 3-phenoxy | 2 | CH₃ | OCH₃ | N | |
| 224 | 5-Cl | 3-phenoxy | 2 | CH₃ | OCH₃ | CH | |
| 225 | H | 3-(3'-fluorophenoxy) | 2 | CH₃ | OCH₃ | CH | |
| 226 | H | 3-(3'-fluorophenoxy) | 2 | OCH₃ | OCH₃ | N | |
| 227 | H | 3-(3'-fluorophenoxy) | 2 | CH₃ | OCH₃ | N | |
| 228 | H | 3-(3'-fluorophenoxy) | 2 | OCH₃ | OCH₃ | CH | |
| 229 | H | 3-(2'-fluorophenoxy) | 2 | CH₃ | OCH₃ | CH | |
| 230 | H | 3-(2'-fluorophenoxy) | 2 | CH₃ | OCH₃ | N | |
| 231 | H | 3-phenylthio | 2 | CH₃ | OCH₃ | N | |
| 232 | H | 3-phenylthio | 2 | OCH₃ | OCH₃ | N | |
| 233 | H | 3-phenylthio | 2 | CH₃ | OCH₃ | CH | |
| 234 | H | 3-phenylthio | 2 | OCH₃ | OCH₃ | CH | |
| 235 | H | 2-S—CH₂—CH=CH₂ | 3 | OCH₃ | OCHF₂ | CH | 136–138° |
| 236 | H | 2-S—CH₂—CH=CH₂ | 3 | CH₃ | OCHF₂ | CH | |
| 237 | H | 2-S—CH₂—CH=CH₂ | 3 | OCH₃ | Cl | CH | |
| 238 | H | 2-S—CH₂—CH=CH₂ | 3 | OCH₃ | N(CH₃)₂ | CH | |
| 239 | H | 2-S—CH₂—CH=CH₂ | 3 | OCHF₂ | OCHF₂ | CH | |
| 240 | H | 2-S—CH₂—CH=CH₂ | 3 | OCHF₂ | OC₂H₅ | CH | |
| 241 | H | 2-S—CH₂—CH=CH₂ | 3 | OCHF₂ | Cl | CH | |
| 242 | H | 2-S—CH₂—CH=CH₂ | 3 | OCH₃ | N(CH₃)₂ | N | |
| 243 | H | 2-S—CH₂—CH=CH₂ | 3 | OCH₃ | OCH₂CF₃ | N | |
| 244 | H | 2-NHCH₂CH=CH₂ | 3 | CH₃ | OCH₃ | N | 130–133° |
| 245 | H | 2-NHCH₂CH=CH₂ | 3 | OCH₃ | OCH₃ | N | 132–134° |
| 246 | H | 2-NHCH₂CH=CH₂ | 3 | OCH₃ | N(CH₃)₂ | N | |
| 247 | H | 2-NHCH₂CH=CH₂ | 3 | OCH₃ | OCH₂CF₃ | N | |
| 248 | H | 2-NHCH₂CH=CH₂ | 3 | CH₃ | CH₃ | CH | 141–143° |
| 249 | H | 2-NHCH₂CH=CH₂ | 3 | CH₃ | OCH₃ | CH | 150–151° |
| 250 | H | 2-NHCH₂CH=CH₂ | 3 | OCH₃ | OCH₃ | CH | |
| 251 | H | 2-NHCH₂CH=CH₂ | 3 | CH₃ | OCHF₂ | CH | 121–123° |
| 252 | H | 2-NHCH₂CH=CH₂ | 3 | OCH₃ | OCHF₂ | CH | |
| 253 | H | 2-NHCH₂CH=CH₂ | 3 | OCHF₂ | OCHF₂ | CH | |
| 254 | H | 2-NHCH₂CH=CH₂ | 3 | OCHF₂ | OC₂H₅ | CH | |
| 255 | H | 2-NHCH₂CH=CH₂ | 3 | OCHF₂ | Cl | CH | |
| 256 | H | 2-NHCH₂CH=CH₂ | 3 | OCH₃ | Cl | CH | |
| 257 | H | 2-N(CH₃)CH₂CH=CH₂ | 3 | CH₃ | OCH₃ | N | |
| 258 | H | 2-N(CH₃)CH₂CH=CH₂ | 3 | CH₃ | OC₂H₅ | N | |
| 259 | H | 2-N(CH₃)CH₂CH=CH₂ | 3 | OCH₃ | OCH₃ | N | |
| 260 | H | 2-N(CH₃)CH₂CH=CH₂ | 3 | OCH₃ | OCH₂CF₃ | N | |
| 261 | H | 2-N(CH₃)CH₂CH=CH₂ | 3 | OCH₃ | N(CH₃)₂ | N | |
| 262 | H | 2-N(CH₃)CH₂CH=CH₂ | 3 | CH₃ | OCH₃ | CH | |
| 263 | H | 2-N(CH₃)C₂H₄CN | 3 | CH₃ | OCHF₂ | CH | |
| 264 | H | 2-N(CH₃)C₂H₄CN | 3 | OCH₃ | Cl | CH | |
| 265 | H | 2-N(CH₃)C₂H₄CN | 3 | OCHF₂ | OCHF₂ | CH | |
| 266 | H | 2-N(CH₃)C₂H₄CN | 3 | CH₃ | CH₃ | CH | |
| 267 | H | 2-piperidino | 3 | CH₃ | OCHF₂ | CH | 163–167° |
| 268 | H | 2-piperidino | 3 | OCH₃ | Cl | CH | |
| 269 | H | 2-piperidino | 3 | CH₃ | CH₃ | CH | |
| 270 | H | 2-(4'-benzyl-piperazino) | 3 | CH₃ | OCH₃ | N | 200–202° |
| 271 | H | 2-(4'-benzyl-piperazino) | 3 | CH₃ | OCH₃ | CH | 176–178° |
| 272 | H | 2-(4'-benzyl-piperazino) | 3 | CH₃ | OCHF₂ | N | 230° dec. |
| 273 | H | 2-OCH₂CH=CH₂ | 3 | CH₃ | OC₂H₅ | N | 110–112° |
| 274 | H | 2-OCH₂CH=CH₂ | 3 | OCH₃ | OCHF₂ | CH | |
| 275 | H | 2-OCH₂CH=CH₂ | 3 | OCHF₂ | OCHF₂ | CH | |
| 276 | H | 2-OCHC(CH₃)=CH₂ | 3 | CH₃ | OC₂H₅ | N | |
| 277 | H | 2-OCHC(CH₃)=CH₂ | 3 | OCH₃ | OCHF₂ | CH | |
| 278 | H | 2-OCHC(CH₃)=CH₂ | 3 | OCHF₂ | OCHF₂ | CH | |
| 279 | H | 2-OCH₂CH=CHCH₃ | 3 | CH₃ | OC₂H₅ | N | 131–134° |
| 280 | H | 2-OCH₂CH=CHCH₃ | 3 | OCH₃ | Cl | CH | 157–160° |
| 281 | H | 2-OCH₂CH=CHCH₃ | 3 | OCH₃ | OCHF₂ | CH | |
| 282 | H | 2-OCH₂CH=CHCH₃ | 3 | OCHF₂ | OCHF₂ | CH | |
| 283 | H | 2-OCH₂C≡CH | 3 | CH₃ | OC₂H₅ | N | |
| 284 | H | 2-OCH₂C≡CH | 3 | OCH₃ | Cl | CH | |
| 285 | H | 2-OCH₂C≡CH | 3 | OCH₃ | OCHF₂ | CH | |

-continued

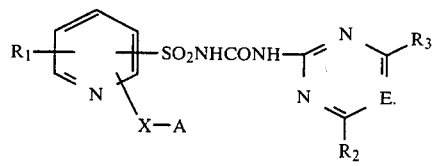

| No. | R₁ | X—A | Position −SO₂− | R₂ | R₃ | E | m.p. °C. |
|---|---|---|---|---|---|---|---|
| 286 | H | 2-OCHC≡CH | 3 | OCHF₂ | OCHF₂ | CH | |
| 287 | H | 2-OCH₂CHClCH₂Cl | 3 | CH₃ | OCH₃ | N | 135–138° |
| 288 | H | 2-OCH₂CHClCH₂Cl | 3 | CH₃ | OC₂H₅ | N | |
| 289 | H | 2-OCH₂CHClCH₂Cl | 3 | C₂H₅ | OCH₃ | N | |
| 290 | H | 2-OCH₂CHClCH₂Cl | 3 | OCH₃ | OCH₃ | N | |
| 291 | H | 2-OCH₂CHClCH₂Cl | 3 | OCH₃ | OCH₂CF₃ | N | |
| 292 | H | 2-OCH₂CHClCH₂Cl | 3 | OCH₃ | N(CH₃)₂ | N | |
| 293 | H | 2-OCH₂CHClCH₂Cl | 3 | CH₃ | OCH₃ | CH | |
| 294 | H | 2-OCH₂CHClCH₂Cl | 3 | CH₃ | OCHF₂ | CH | |
| 295 | H | 2-OCH₂CHClCH₂Cl | 3 | CH₃ | CH₃ | CH | |
| 296 | H | 2-OCH₂CHClCH₂Cl | 3 | OCH₃ | Cl | CH | |
| 297 | H | 2-OCH₂CHClCH₂Cl | 3 | OCH₃ | OCH₃ | CH | |
| 298 | H | 2-OCH₂CHClCH₂Cl | 3 | OCH₃ | OCHF₂ | CH | |
| 299 | H | 2-OCH₂CHClCH₂Cl | 3 | OCH₃ | N(CH₃)₂ | CH | |
| 300 | H | 2-OCH₂CHClCH₂Cl | 3 | OCHF₂ | OCHF₂ | CH | |
| 301 | H | 2-OCH₂CHClCH₂Cl | 3 | OCHF₂ | OC₂H₅ | CH | |
| 302 | H | 2-OCH₂CHClCH₂Cl | 3 | OCHF₂ | Cl | CH | |
| 303 | H | 2-OCH₂CHBrCH₂Br | 3 | CH₃ | OCH₃ | N | |
| 304 | H | 2-OCH₂CHBrCH₂Br | 3 | CH₃ | OC₂H₅ | N | |
| 305 | H | 2-OCH₂CHBrCH₂Br | 3 | C₂H₅ | OCH₃ | N | |
| 306 | H | 2-OCH₂CHBrCH₂Br | 3 | OCH₃ | OCH₃ | N | |
| 307 | H | 2-OCH₂CHBrCH₂Br | 3 | OCH₃ | OCH₂CF₃ | N | |
| 308 | H | 2-OCH₂CHBrCH₂Br | 3 | OCH₃ | N(CH₃)₂ | N | |
| 309 | H | 2-OCH₂CHBrCH₂Br | 3 | CH₃ | OCH₃ | CH | |
| 310 | H | 2-OCH₂CHBrCH₂Br | 3 | CH₃ | OCHF₂ | CH | |
| 311 | H | 2-OCH₂CHBrCH₂Br | 3 | CH₃ | CH₃ | CH | |
| 312 | H | 2-OCH₂CHBrCH₂Br | 3 | OCH₃ | Cl | CH | |
| 313 | H | 2-OCH₂CHBrCH₂Br | 3 | OCH₃ | OCH₃ | CH | 148–150° |
| 314 | H | 2-OCH₂CHBrCH₂Br | 3 | OCH₃ | OCHF₂ | CH | |
| 315 | H | 2-OCH₂CHBrCH₂Br | 3 | OCH₃ | N(CH₃)₂ | CH | |
| 316 | H | 2-OCH₂CHBrCH₂Br | 3 | OCHF₂ | OCHF₂ | CH | |
| 317 | H | 2-OCH₂CHBrCH₂Br | 3 | OCHF₂ | OC₂H₅ | CH | |
| 318 | H | 2-OCH₂CHBrCH₂Br | 3 | OCHF₂ | Cl | CH | |
| 319 | H | 2-OCH₂CCl(CH₃)CH₂Cl | 3 | CH₃ | OCH₃ | N | |
| 320 | H | 2-OCH₂CCl(CH₃)CH₂Cl | 3 | CH₃ | OC₂H₅ | N | |
| 321 | H | 2-OCH₂CCl(CH₃)CH₂Cl | 3 | C₂H₅ | OCH₃ | N | |
| 322 | H | 2-OCH₂CCl(CH₃)CH₂Cl | 3 | OCH₃ | OCH₃ | N | |
| 323 | H | 2-OCH₂CCl(CH₃)CH₂Cl | 3 | OCH₃ | OCH₂CF₃ | N | |
| 324 | H | 2-OCH₂CCl(CH₃)CH₂Cl | 3 | OCH₃ | N(CH₃)₂ | N | |
| 325 | H | 2-OCH₂CCl(CH₃)CH₂Cl | 3 | CH₃ | OCH₃ | CH | |
| 326 | H | 2-OCH₂CCl(CH₃)CH₂Cl | 3 | CH₃ | OCHF₂ | CH | |
| 327 | H | 2-OCH₂CCl(CH₃)CH₂Cl | 3 | CH₃ | CH₃ | CH | |
| 328 | H | 2-OCH₂CCl(CH₃)CH₂Cl | 3 | OCH₃ | Cl | CH | |
| 329 | H | 2-OCH₂CCl(CH₃)CH₂Cl | 3 | OCH₃ | OCH₃ | CH | |
| 330 | H | 2-OCH₂CCl(CH₃)CH₂Cl | 3 | OCH₃ | OCHF₂ | CH | |
| 331 | H | 2-OCH₂CCl(CH₃)CH₂Cl | 3 | OCH₃ | N(CH₃)₂ | CH | |
| 332 | H | 2-OCH₂CCl(CH₃)CH₂Cl | 3 | OCHF₂ | OCHF₂ | CH | |
| 333 | H | 2-OCH₂CCl(CH₃)CH₂Cl | 3 | OCHF₂ | OC₂H₅ | CH | |
| 334 | H | 2-OCH₂CCl(CH₃)CH₂Cl | 3 | OCHF₂ | Cl | CH | |
| 335 | H | 2-OCH₂CBr(CH₃)CH₂Br | 3 | CH₃ | OCH₃ | N | |
| 336 | H | 2-OCH₂CBr(CH₃)CH₂Br | 3 | CH₃ | OC₂H₅ | N | |
| 337 | H | 2-OCH₂CBr(CH₃)CH₂Br | 3 | C₂H₅ | OCH₃ | N | |
| 338 | H | 2-OCH₂CBr(CH₃)CH₂Br | 3 | OCH₃ | OCH₃ | N | |
| 339 | H | 2-OCH₂CBr(CH₃)CH₂Br | 3 | OCH₃ | OCH₂CF₃ | N | |
| 340 | H | 2-OCH₂CBr(CH₃)CH₂Br | 3 | OCH₃ | N(CH₃)₂ | N | |
| 341 | H | 2-OCH₂CBr(CH₃)CH₂Br | 3 | CH₃ | OCH₃ | CH | |
| 342 | H | 2-OCH₂CBr(CH₃)CH₂Br | 3 | CH₃ | OCHF₂ | CH | |
| 343 | H | 2-OCH₂CBr(CH₃)CH₂Br | 3 | CH₃ | CH₃ | CH | |
| 344 | H | 2-OCH₂CBr(CH₃)CH₂Br | 3 | OCH₃ | Cl | CH | |
| 345 | H | 2-OCH₂CBr(CH₃)CH₂Br | 3 | OCH₃ | OCH₃ | CH | |
| 346 | H | 2-OCH₂CBr(CH₃)CH₂Br | 3 | OCH₃ | OCHF₂ | CH | |
| 347 | H | 2-OCH₂CBr(CH₃)CH₂Br | 3 | OCH₃ | N(CH₃)₂ | CH | |
| 348 | H | 2-OCH₂CBr(CH₃)CH₂Br | 3 | OCHF₂ | OCHF₂ | CH | |
| 349 | H | 2-OCH₂Cbr(CH₃)CH₂Br | 3 | OCHF₂ | OC₂H₅ | CH | |
| 350 | H | 2-OCH₂CBr(CH₃)CH₂Br | 3 | OCHF₂ | Cl | CH | |
| 351 | H | 2-OCH₂(CHCl)₂CH₃ | 3 | CH₃ | OCH₃ | N | |
| 352 | H | 2-OCH₂(CHCl)₂CH₃ | 3 | CH₃ | OC₂H₅ | N | |
| 353 | H | 2-OCH₂(CHCl)₂CH₃ | 3 | C₂H₅ | OCH₃ | N | |
| 354 | H | 2-OCH₂(CHCl)₂CH₃ | 3 | OCH₃ | OCH₃ | N | |
| 355 | H | 2-OCH₂(CHCl)₂CH₃ | 3 | OCH₃ | OCH₂CF₃ | N | |
| 356 | H | 2-OCH₂(CHCl)₂CH₃ | 3 | OCH₃ | N(CH₃)₂ | N | |

-continued

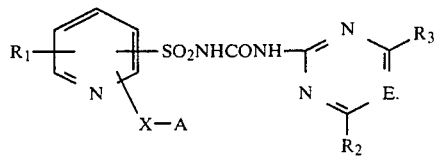

| No. | R₁ | X—A | Position —SO₂— | R₂ | R₃ | E | m.p. °C. |
|---|---|---|---|---|---|---|---|
| 357 | H | 2-OCH₂(CHCl)₂CH₃ | 3 | CH₃ | OCH₃ | CH | |
| 358 | H | 2-OCH₂(CHCl)₂CH₃ | 3 | CH₃ | OCHF₂ | CH | |
| 359 | H | 2-OCH₂(CHCl)₂CH₃ | 3 | CH₃ | CH₃ | CH | 140–143° |
| 360 | H | 2-OCH₂(CHCl)₂CH₃ | 3 | OCH₃ | Cl | CH | |
| 361 | H | 2-OCH₂(CHCl)₂CH₃ | 3 | OCH₃ | OCH₃ | CH | |
| 362 | H | 2-OCH₂(CHCl)₂CH₃ | 3 | OCH₃ | OCHF₂ | CH | |
| 363 | H | 2-OCH₂(CHCl)₂CH₃ | 3 | OCH₃ | N(CH₃)₂ | CH | |
| 364 | H | 2-OCH₂(CHCl)₂CH₃ | 3 | OCHF₂ | OCHF₂ | CH | |
| 365 | H | 2-OCH₂(CHCl)₂CH₃ | 3 | OCHF₂ | OC₂H₅ | CH | |
| 366 | H | 2-OCH₂(CHCl)₂CH₃ | 3 | OCHF₂ | Cl | CH | |
| 367 | H | 2-OCH₂(CHBr)₂CH₃ | 3 | CH₃ | OCH₃ | N | |
| 368 | H | 2-OCH₂(CHBr)₂CH₃ | 3 | CH₃ | OC₂H₅ | N | |
| 369 | H | 2-OCH₂(CHBr)₂CH₃ | 3 | C₂H₅ | OCH₃ | N | |
| 370 | H | 2-OCH₂(CHBr)₂CH₃ | 3 | OCH₃ | OCH₃ | N | |
| 371 | H | 2-OCH₂(CHBr)₂CH₃ | 3 | OCH₃ | OCH₂CF₃ | N | |
| 372 | H | 2-OCH₂(CHBr)₂CH₃ | 3 | OCH₃ | N(CH₃)₂ | N | |
| 373 | H | 2-OCH₂(CHBr)₂CH₃ | 3 | CH₃ | OCH₃ | CH | |
| 374 | H | 2-OCH₂(CHBr)₂CH₃ | 3 | CH₃ | OCHF₂ | CH | |
| 375 | H | 2-OCH₂(CHBr)₂CH₃ | 3 | CH₃ | CH₃ | CH | |
| 376 | H | 2-OCH₂(CNBr)₂CH₃ | 3 | OCH₃ | Cl | CH | |
| 377 | H | 2-OCH₂(CHBr)₂CH₃ | 3 | OCH₃ | OCH₃ | CH | |
| 378 | H | 2-OCH₂(CHBr)₂CH₃ | 3 | OCH₃ | OCHF₂ | CH | |
| 379 | H | 2-OCH₂(CHBr)₂CH₃ | 3 | OCH₃ | N(CH₃)₂ | CH | |
| 380 | H | 2-OCH₂(CHBr)₂CH₃ | 3 | OCHF₂ | OCHF₂ | CH | |
| 381 | H | 2-OCH₂(CHBr)₂CH₃ | 3 | OCHF₂ | OC₂H₅ | CH | |
| 382 | H | 2-OCH₂(CHBr)₂CH₃ | 3 | OCHF₂ | Cl | CH | |
| 383 | H | 2-OCH₂CH=CH₂ | 3 | OCH₃ | Cl | CH | 151–161° |
| 384 | H | 2-OCH₂CH=CH₂ | 3 | OC₂H₅ | OC₂H₅ | N | 114–116° |
| 385 | H | 2-OCH₂CH=CHCH₃ | 3 | OC₂H₅ | OC₂H₅ | N | 106–108° |
| 386 | H | 2-OCH₂C(CH₃)=CH₂ | 3 | OC₂H₅ | CH₃ | N | 117–118° |
| 387 | H | 2-OCH₂C(CH₃)=CH₂ | 3 | OCH₃ | Cl | CH | 142–145° |
| 388 | H | 2-OCH₂C(CH₃)=CH₂ | 3 | OC₂H₅ | OC₂H₅ | N | 95–98° |
| 389 | H | 2-N(CH₂CH=CH₂)₂ | 3 | OCH₃ | N(CH₃)₂ | N | 153–154° |
| 390 | H | 2-N(CH₂CH=CH₂)₂ | 3 | OCH₃ | Cl | CH | 140–141° |
| 391 | H | 2-piperidino | 3 | OC₂H₅ | CH₃ | N | 152–157° |
| 392 | H | 2-piperidino | 3 | OCH₃ | N(CH₃)₂ | N | 210–211° |
| 393 | H | 2-piperidino | 3 | OC₂H₅ | OC₂H₅ | N | 121–124° |
| 394 | H | 2-piperidino | 3 | OCH₃ | OCH₂CF₃ | N | 133–135° |
| 395 | H | 2-morpholino | 3 | OC₂H₅ | CH₃ | N | 107–110° |
| 396 | H | 2-morpholino | 3 | OCH₃ | N(CH₃)₂ | N | 153–157° |
| 397 | H | 2-morpholino | 3 | OCH₃ | OCH₂CF₃ | N | 92–95° |
| 398 | H | 2-morpholino | 3 | CH₃ | CH₃ | CH | 180–183° |
| 399 | H | 2-morpholino | 3 | OC₂H₅ | OC₂H₅ | N | 140–143° |
| 400 | H | 2-morpholino | 3 | OCH₃ | Cl | CH | 187–193° |

The following starting pyridylsulfonamides of the formula II are prepared in accordance with Example 1:

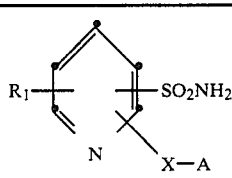

| R₁ | X—A | Position —SO₂NH₂ | m.p. |
|---|---|---|---|
| H | 2-OC₂H₄OCH₃ | 3 | 102–103° C. |
| H | 2-OCH₂CH=CH₂ | 3 | 121–121.5° C. |
| H | 2-OCH₂C≡CH | 3 | 145–47° C. |
| H | 2-OC(CH₃)=CH₂ | 3 | 65–66° C. |
| H | 2-OCH₂—CH=C(CH₃)₂ | 3 | |
| H | 2-OCH₂CH=CHCH₃ | 3 | 225–226° C. |
| H | 2-OCHF₂ | 3 | |
| H | 2-OCH₂CF₃ | 3 | |

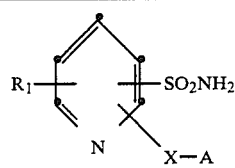

| R₁ | X—A | Position —SO₂NH₂ | m.p. |
|---|---|---|---|
| H | 3-OCHF₂ | 2 | |
| H | 2-OC₂H₄Cl | 3 | |
| H | 2-OCF₂CF₃ | 3 | |
| H | 2-OC₂H₄OC₂H₅ | 3 | |
| H | 2-OC₂H₄OCH₂CH=CH₂ | 3 | |
| H | 2-OCH(CH₃)CH₂OCH₃ | 3 | |
| 6-CH₃ | 2-OC₂H₄OCH₃ | 3 | |
| 6-CH₃ | 2-OCH₂CH=CH₂ | 3 | |
| 6-CH₃ | 2-OCH₂C≡CH | 3 | |
| 6-CH₃ | 2-OCHF₂ | 3 | |
| 6-CH₃ | 2-OC₂H₄Cl | 3 | |

-continued

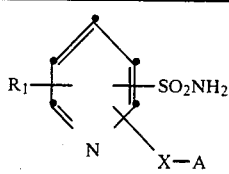

| $R_1$ | X—A | Position —$SO_2NH_2$ | m.p. |
|---|---|---|---|
| 6-$CH_3$ | 4-$OC_2H_4OCH_3$ | 3 | |
| 6-$CH_3$ | 4-$OCH_2CH=CH_2$ | 2 | |
| 6-$CH_3$ | 4-$OCH_2C\equiv CH$ | 3 | |
| 6-$CH_3$ | 4-$OC_2H_4Cl$ | 3 | |
| H | 2-$SCH_2CH=CH_2$ | 3 | |
| H | 2-$OCF_2CHF_2$ | 3 | |
| H | 2-$SCHF_2$ | 3 | |
| H | 2-$SCH_2C\equiv CH$ | 3 | |
| H | 2-$SO_2C_2H_4OCH_3$ | 3 | |
| H | 2-$SO_2CH_2CH=CH_2$ | 3 | |
| H | 2-$SO_2CH_2C\equiv CH$ | 3 | |
| H | 2-$NH_2$ | 3 | 175–176° C. |
| H | 2-$NHCH_3$ | 3 | 171–172° C. |
| H | 2-$N(CH_3)_2$ | 3 | 100–102° C. |
| H | 2-$N(CH_2CH=CH_2)$ | 3 | 90–91° C. |
| H | 2-piperidino | 3 | 155–156° C. |
| H | 2-morpholino | 3 | 183–184° C. |
| H | 2-(4′-benzylpiperazino) | 3 | 164–165° C. |
| H | 2-(4′-methylpiperazino) | 3 | 130–134° C. |
| H | 2-$N(CH_3)C_2H_4CN$ | 3 | |
| H | 2-$N(C_2H_5)C_2H_4CN$ | 3 | |
| H | 2-phenoxy | 3 | 176–178° C. |
| H | 2-$OC_2H_4OCH_3$ | 3 | |
| H | 2-$OCH_2CH=CH_2$ | 3 | 144–146° C. |
| H | 2-$OCH_2C(CH_3)=CH_2$ | 3 | |
| H | 2-$OCH_2CH=CHCH_3$ | 3 | |
| H | 2-S—$CH_2CH=CH_2$ | 3 | |
| H | 2-O—$CH_2CH=C(CH_3)_2$ | 3 | |
| 6-$CH_3$ | 2-O—$CH_2=CH_2$ | 3 | |
| H | 2-$OCH_2C\equiv CH$ | 3 | |
| H | $N(CH_3)_2$ | 3 | |
| H | $NHCH_2CH=CH_2$ | 3 | 98–99° |

EXAMPLE 5

Formulation examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silocone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

EXAMPLE 6

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the plants is assessed according to the following rating:

1: plants have not emerged or are totally withered
2-3: very pronounced action
4-6: medium action
7-8: weak action
9: no action (as untreated controls).

Preemergence action:
Concentration of the test compound emulsion: 70.8 ppm

| Test plant Compound | Nasturtium | Stellaria | Agrostis | Digitaria |
|---|---|---|---|---|
| 1 | 2 | 2 | 2 | 2 |
| 8 | 1 | 1 | 2 | 2 |
| 9 | 1 | 1 | 1 | 2 |
| 13 | 1 | 1 | 2 | 2 |
| 14 | 1 | 1 | 2 | 1 |
| 16 | 2 | 1 | 3 | 3 |
| 17 | 2 | 1 | 1 | 1 |
| 22 | 1 | 1 | 1 | 1 |
| 24 | 2 | 1 | 2 | 2 |
| 25 | 3 | 3 | 4 | 5 |
| 30 | 1 | 1 | 2 | 2 |
| 33 | 2 | 2 | 3 | 4 |
| 38 | 1 | 1 | 2 | 2 |
| 41 | 3 | 3 | 3 | 7 |
| 48 | 2 | 2 | 4 | 4 |
| 153 | 1 | 1 | 2 | 2 |
| 161 | 2 | 1 | 2 | 2 |
| 162 | 2 | 1 | 2 | 2 |
| placebos without active ingredient | 9 | 9 | 9 | 9 |

EXAMPLE 7

Test of selectivity in preemergence application

Seeds of dicot and monocot weeds and cultivated plants are sown in a greenhouse in pots of 11 cm diameter. Immediately afterwards the surface of the soil is treated with an aqueous dispersion or solution of the test compound. Concentrations of 0.250, 0.125 and 0.06 kg a.i./ha are employed. The pots are then kept in the greenhouse at 22°-25° C. and 50-70% relative humidity. The test is evaluated after 3 weeks and the activity is determined in accordance with the same rating as in Example 6.

Test results (preemergence)

| Activity Rate of application in kg a.i./ha | Compound 1 | | Compound 25 | | Compound 33 | | Compound 38 | |
|---|---|---|---|---|---|---|---|---|
| Test plant | 0.125 | 0.03 | 0.125 | 0.03 | 0.125 | 0.03 | 0.125 | 0.03 |
| barley | 7 | 9 | 8 | 9 | 7 | 7 | 2 | 3 |
| wheat | 9 | 9 | 9 | 9 | 9 | 9 | 2 | 3 |
| maize | 8 | 9 | 9 | 9 | 9 | 9 | 2 | 9 |
| rice | 5 | 7 | 7 | 8 | 7 | 9 | 4 | 7 |
| *Alopecuvus myos.* | 5 | 6 | 4 | 4 | 4 | 4 | 2 | 2 |
| Echinochloa c.g. | 6 | 7 | 5 | 7 | 7 | 9 | 2 | 4 |
| soybeans | 5 | 7 | 3 | 4 | 3 | 4 | 4 | 9 |
| cotton | 4 | 7 | 3 | 4 | 3 | 4 | 4 | 8 |
| *Amaranthus vet.* | 2 | 2 | 2 | 3 | 2 | 2 | 3 | 3 |
| Chenopodium Sp. | 3 | 4 | 4 | 4 | 3 | 6 | 3 | 3 |
| Sinapsis | 2 | 4 | 2 | 2 | 2 | 2 | 2 | 3 |
| Stellaria | 3 | 4 | 2 | 3 | 2 | 2 | 2 | 2 |
| *Chrysanth. leuc.* | 2 | 4 | 2 | 3 | 2 | 2 | 2 | 2 |
| *Galium aparine* | 2 | 5 | 2 | 3 | 2 | 2 | 3 | 3 |
| *Viola tricolor* | 2 | 3 | 2 | 2 | 2 | 2 | 3 | 5 |
| Veronica Sp. | 1 | 2 | 2 | 2 | 2 | 2 | 2 | 2 |

EXAMPLE 8

Postemergence herbicidal action (contact action)

A number of weeds and cultivated plants, both monocots and dicots, are sprayed postemergence, in the 4- to 6-leaf stage, with an aqueous dispersion of test compound at rates of application of 0.5 kg of a.i./ha, and then kept at 24°-26° and 45-60% relative humidity. The test is evaluated 15 days after treatment using the same rating as in the preemergence test.

Postemergence activity:
Rate of application: 0.5 kg of active ingredient per hectare

| Compound | Avena Sativa | Setaria italica | Lolium perenne | Solanum lycopers. | Sivapis alba | Stellaria media | Phoseulus vulgaris |
|---|---|---|---|---|---|---|---|
| 1 | 8 | 6 | 3 | 1 | 1 | 2 | 3 |

-continued

| | Postemergence activity: Rate of application: 0.5 kg of active ingredient per hectare | | | | | | |
|---|---|---|---|---|---|---|---|
| Compound | Avena Sativa | Setaria italica | Lolium perenne | Solanum lycopers. | Sivapis alba | Stellaria media | Phoseulus vulgaris |
| 2 | 3 | 5 | 5 | 3 | 2 | 5 | 7 |
| 9 | 5 | 7 | 3 | 2 | 2 | 3 | 3 |
| 14 | 2 | 5 | 3 | 2 | 2 | 4 | 3 |
| 17 | 5 | 4 | 3 | 2 | 2 | 3 | 3 |
| 22 | 3 | 5 | 4 | 2 | 2 | 3 | 3 |

EXAMPLE 9

Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 10

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 6 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

EXAMPLE 11

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 100 g of active ingredient per hectare. Evaluation of the growth of the cereals is made 21 days after application. A comparison with untreated controls shows that the growth of cereal plants treated with compounds of the formula I is significantly reduced (60-90% of the controls) and that the diameter of the stalks has in some cases increased.

EXAMPLE 12

Growth inhibition of grasses

Seeds of grasses Lolium perenne, Poa pratensis, Festuca ovina, and Cynodon dactylon are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10-30% in comparison with untreated controls.

What is claimed is:

1. An N-pyridylsulfonyl-N'-pyrimidinylurea of the formula

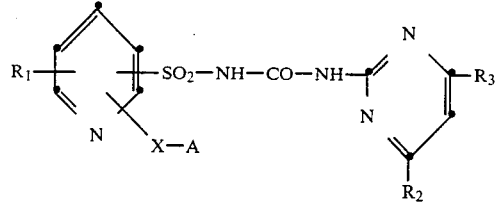

wherein

A is a $C_3$-$C_6$ alkynyl radical, or a $C_1$-$C_6$ alkyl radical which is substituted by halogen or $C_1$-$C_4$ alkoxy, or A is a $C_2$-$C_4$ alkenyl radical which is unsubstituted or substituted by halogen or $C_1$-$C_4$ alkoxy, or A is a phenyl radical which is unsubstituted or substituted by halogen, cyano, nitro, $C_1$-$C_4$ alkyl, $C_1$-$C_4$ haloalkyl or —X—$C_1$-$C_4$ alkyl, or A—X— forms an amino radical —$NR_6R_7$, $R_1$ is hydrogen, halogen or $C_1$-$C_4$ alkyl, $R_2$ is $C_1$-$C_3$ alkyl which is unsubstituted or substituted by 1 to 3 halogen atoms, or is $C_1$-$C_3$ alkoxy, $R_3$ is hydrogen, halogen, an amino group —$NR_4R_5$, or $C_1$-$C_3$ alkyl which is unsubstituted or substituted by 1 to 3 halogen atoms, or is $C_1$-$C_4$ alkoxy which is unsubstituted or substituted by methoxy, ethoxy or 1 to 3 halogen atoms, $R_4$ is hydrogen or methyl, $R_5$ is hydrogen, $C_1$-$C_2$ alkyl or methoxy, $R_6$ and $R_7$ are each independently hydrogen, $C_1$-$C_4$ alkyl, $C_3$-$C_6$ alkenyl, $C_3$-$C_6$ alkynyl, or both together with the nitrogen atom to which they are attached also form a saturated 5- or 6-membered heterocyclic ring system which may also contain oxygen, sulfur or an —$NR_8$ radical, $R_8$ is hydrogen, $C_1$-$C_4$ alkyl or benzyl, and X is oxygen or sulfur, or a salt thereof.

2. An N-pyridylsulfonyl-N'-pyrimidinylurea according to claim 1, wherein $R_1$ is hydrogen.

3. An N-pyridylsulfonyl-N'-pyrimidinylurea according to claim 1, wherein $R_1$ is hydrogen, —X—A is in the 2-position and the —$SO_2$— group in the 3-position of the pyridyl ring.

4. An N-pyridylsulfonyl-N'-pyrimidinylurea according to claim 1, wherein A is $C_3$–$C_4$ alkenyl or $C_3$–$C_4$ alkynyl and $R_1$ is hydrogen.

5. A herbicidal and plant growth regulating composition which contains an effective amount of an N-pyridylsulfonyl-N'-pyrimidinylurea according to claim 1, together with an inert carrier and/or other inert adjuvants.

6. A method of controlling undesired plant growth, which comprises applying to the plants or area of undesired plant growth an effective amount of an N-pyridylsulfonyl-N'-pyrimidinylurea according to claim 1, or of a composition containing said compound.

7. A method of inhibiting plant growth, which comprises applying to the plants an effective amount of an N-pyridylsulfonyl-N'-pyrimidinylurea according to claim 1, or of a composition containing said compound.

8. A method according to claim 6 of selectively controlling weeds pre- or postemergence in crops of useful plants, which method comprises applying to the crops or crop area an effective amount of an N-pyridylsulfonyl-N'-pyrimidinylurea according to claim 1, or of a composition containing said compound.

9. A method according to claim 7 of inhibiting plant growth beyond the 2-leaf stage preemergence, which method comprises applying to the emerging plants an effective amount of an N-pyridylsulfonyl-N'-pyrimidinylurea according to claim 1, or a composition containing said compound.

10. A method according to claim 8, wherein said crops are sugar cane, cereals, maize, rice, soybeans or cotton.

11. A method of inhibiting the growth of cultivated plants to obtain an increase in yield, which comprises applying to the plants an effective amount of an N-pyridylsulfonyl-N'-pyrimidinylurea according to claim 1, or of a composition containing said compound.

12. A method according to claim 11, wherein said cultivated plants are soybeans.

13. A method according to claim 7, wherein said plants are cover crop leguminosae.

14. N-[2-(2-methylallyloxy)-pyridin-3-ylsulfonyl]-N'-(4-methoxy-6-methylpyrimidin-2-yl)urea according to claim 6.

15. N-[2-(2-methylallyloxy)-pyridin-3-ylsulfonyl]-N'-(4-difluoromethoxy-6-methylpyrimidin-2-yl)urea according to claim 6.

16. N-[2-(2-butenyloxy)-pyridin-3-ylsulfonyl]-N'-(4,6-dimethylpyrimidin-2-yl)urea according to claim 6.

17. An N-pyridylsulfonyl-N'-pyrimidinylurea according to claim 1 of the formula

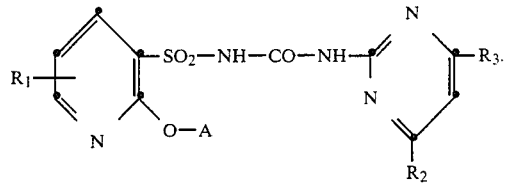

* * * * *

REEXAMINATION CERTIFICATE (1013th)
United States Patent [19]
Föry et al.

[11] B1 4,579,583
[45] Certificate Issued  Feb. 14, 1989

[54] NOVEL SULFONYLUREAS

[75] Inventors: Werner Föry, Basel; Karl Gass, Magden; Willy Meyer, Riehen, all of Switzerland

[73] Assignee: Ciba-Geigy Corporation, Ardsley, N.Y.

Reexamination Request:
No. 90/001,468, Mar. 15, 1988

Reexamination Certificate for:
Patent No.: 4,579,583
Issued: Apr. 1, 1986
Appl. No.: 527,599
Filed: Aug. 29, 1983

[30] Foreign Application Priority Data
Sep. 8, 1982 [CH] Switzerland ............ 5337/82
Apr. 28, 1983 [CH] Switzerland ............ 2283/83

[51] Int. Cl.$^4$ .................... C07D 401/12; A01N 47/36
[52] U.S. Cl. ............................. 71/92; 544/320; 544/324; 544/331; 544/113; 544/122; 544/123; 544/209; 544/212; 71/93
[58] Field of Search ................ 544/331, 320, 324; 71/92

[56] References Cited
U.S. PATENT DOCUMENTS
4,544,401  10/1985  Levitt ......................... 71/92

*Primary Examiner*—Robert Gerstl
*Attorney, Agent, or Firm*—Edward McC. Roberts; Kevin T. Mansfield

[57] ABSTRACT

The invention relates to N-pyridylsulfonyl-N'-pyrimidinyl- and -N'-triazinylureas of the formula I

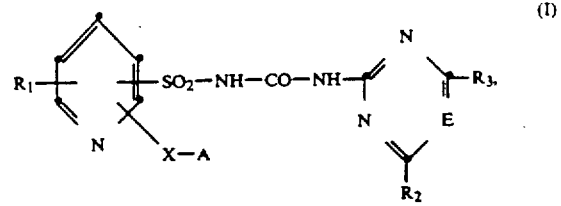

wherein
A is a $C_3$–$C_6$alkynyl radical, a $C_1$–$C_6$alkyl radical which is substituted by halogen, $C_1$–$C_4$alkoxy, $C_1$–$C_4$alkylthio, $C_1$–$C_4$alkylsulfinyl, $C_1$–$C_4$alkylsulfonyl, $C_1$–$C_4$haloalkoxy, $C_1$–$C_4$haloalkylthio, $C_1$–$C_4$haloalkylsulfinyl or $C_1$–$C_4$haloalkylsulfonyl, or is a $C_2$–$C_4$alkenyl radical which is unsubstituted or substituted as for $C_1$–$C_6$alkyl, or is a phenyl radical which is unsubstituted or substituted by halogen, cyano, nitro, $C_1$–$C_4$alkyl, $C_1$–$C_4$haloalkyl, an —X—$C_1$–$C_4$alkyl, $C_1$–$C_4$alkoxycarbonyl, amino, mono- or di-($C_1$–$C_4$alkyl)amino, carbamoyl, mono- or di-($C_1$–$C_4$alkyl)carbamoyl, sulfamoyl, mono- or di-($C_1$–$C_4$alkyl)sulfamoyl radical or A—X— forms an amino radical —$NR_6R_7$,
E is the methine group or nitrogen,
$R_1$ is hydrogen, halogen, $C_1$–$C_4$alkyl, $C_1$–$C_4$alkoxy, $C_1$–$C_4$haloalkyl, $C_1$–$C_4$haloalkoxy, $C_2$14 $C_5$ alkoxyalkoxy, $C_1$–$C_5$alkylthio, $C_1$–$C_5$alkylsulfinyl or $C_1$–$C_5$alkylsulfonyl,
$R_2$ is $C_1$–$C_3$alkyl which is unsubstituted or substituted by 1 to 3 halogen atoms, or is $C_1$–$C_3$alkoxy,
$R_3$ is hydrogen, halogen, an amino group —$NR_4R_5$, or $C_1$–$C_3$alkyl which is unsubstituted or substituted by 1 to 3 halogen atoms, or is $C_1$–$C_4$alkoxy which is unsubstituted or substituted by methoxy, ethoxy or 1 to 3 halogen atoms,
$R_4$ is hydrogen or methyl,
$R_5$ is hydrogen, $C_1$–$C_2$alkyl or methoxy,
$R_6$ and $R_7$ are each independently hydrogen, $C_1$–$C_4$alkyl, $C_3$–$C_6$alkenyl, $C_3$–$C_6$alkynyl, $C_3$–$C_6$alkoxyalkyl, $C_1$–$C_4$cyanoalkyl, or both together with the nitrogen atom to which they are attached also form a saturated 5- or 6-membered heterocyclic ring system which may also contain oxygen, sulfur or an —$NR_8$ radical,
$R_8$ is hydrogen, $C_1$–$C_4$alkyl or benzyl, and
X is oxygen, sulfur, or a sulfinyl or sulfonyl bridge and to the salts thereof with amines, alkali metal bases or alkaline earth metal bases. These compounds have good pre- and postemergence selective herbicidal and growth regulating properties.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–17, dependent on an amended claim, are determined to be patentable.

1. An N-pyridylsulfonyl-N'pyrimidinylurea of the formula

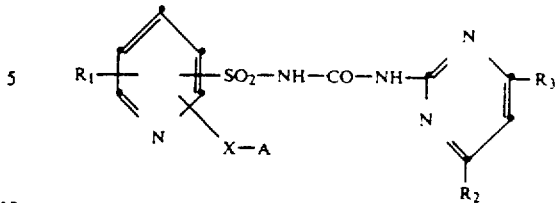

wherein
A is a $C_3$–$C_6$alkynyl radical, or a $C_1$–$C_6$alkyl radical which is substituted by halogen or $C_1$–$C_4$alkoxy, or A is a $C_2$–$C_4$alkenyl radical which is unsubstituted or substituted by halogen or $C_1$–$C_4$alkoxy, or A is a phenyl radical which is unsubstituted or substituted by halogen, cyano, nitro, $C_1$–$C_4$alkyl, $C_1$–$C_4$haloalkyl or —X—$C_1$–$C_4$alkyl [or A—X— forms an amino radical —$NR_6R_7$,]
$R_1$ is hydrogen, halogen or $C_1$–$C_4$alkyl,
$R_2$ is $C_1$–$C_3$alkyl which is unsubstituted or substituted by 1 to 3 halogen atoms, or is $C_1$–$C_3$alkoxy,
$R_3$ is hydrogen, halogen, an amino group —$NR_4R_5$ or $C_1$–$C_3$alkyl which is unsubstituted or substituted by 1 to 3 halogen atoms, or is $C_1$–$C_4$alkoxy which is unsubstituted or substituted by methoxy, ethoxy or 1 to 3 halogen atoms,
$R_4$ is hydrogen or methyl,
$R_5$ is hydrogen, $C_1$–$C_2$alkyl or methoxy,
[$R_6$ and $R_7$ are each independently hydrogen, $C_1$–$C_4$alkyl, $C_3$–$C_6$alkenyl, $C_3$–$C_6$alkynyl, or both together with the nitrogen atom to which they are attached also form a saturated 5- or 6-membered heterocyclic ring system which may also contain oxygen, sulfur or an —$NR_8$ radical,
$R_8$ is hydrogen, $C_1$–$C_4$alkyl or benzyl,] and
X is oxygen or sulfur, or a salt thereof.

* * * * *